:::

(12) United States Patent
Schleicher

(10) Patent No.: US 10,960,132 B1
(45) Date of Patent: Mar. 30, 2021

(54) CLUTCHED DELIVERY DEVICE

(71) Applicant: Verily Life Sciences LLC, South San Francisco, CA (US)

(72) Inventor: Brett Schleicher, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 360 days.

(21) Appl. No.: 15/882,062

(22) Filed: Jan. 29, 2018

Related U.S. Application Data

(60) Provisional application No. 62/452,511, filed on Jan. 31, 2017.

(51) Int. Cl.
*A61M 5/315* (2006.01)
*A61M 5/142* (2006.01)
*A61M 5/145* (2006.01)
*A61M 5/168* (2006.01)

(52) U.S. Cl.
CPC ........ *A61M 5/1452* (2013.01); *A61M 5/1454* (2013.01); *A61M 5/16804* (2013.01); *A61M 2005/14506* (2013.01); *A61M 2005/3151* (2013.01); *A61M 2205/106* (2013.01); *A61M 2207/00* (2013.01)

(58) Field of Classification Search
CPC .............. A61M 5/1452; A61M 5/1454; A61M 5/16804; A61M 5/31501; A61M 2005/14506; A61M 2005/3151
See application file for complete search history.

(56) References Cited

U.S. PATENT DOCUMENTS

| 4,300,554 | A | * | 11/1981 | Hessberg | ............ | A61M 5/1454 |
| | | | | | | 604/135 |
| 5,674,204 | A | | 10/1997 | Chanoch | | |
| 6,348,043 | B1 | * | 2/2002 | Hagen | ................. | A61M 5/1452 |
| | | | | | | 604/131 |
| 8,500,355 | B2 | | 8/2013 | Liu et al. | | |
| 8,651,340 | B2 | | 2/2014 | Lelieveld et al. | | |
| 9,101,718 | B2 | * | 8/2015 | Kiilerich | ............ | A61M 5/31515 |
| 9,211,377 | B2 | | 12/2015 | Kruse et al. | | |
| 2004/0261790 | A1 | | 12/2004 | Joshi et al. | | |
| 2009/0124994 | A1 | | 5/2009 | Roe et al. | | |
| 2013/0338586 | A1 | | 12/2013 | Dickinson et al. | | |

* cited by examiner

*Primary Examiner* — Manuel A Mendez
*Assistant Examiner* — Justin L Zamory
(74) *Attorney, Agent, or Firm* — Kilpatrick Townsend & Stockton LLP

(57) ABSTRACT

In some examples, a fluid delivery device is described. The fluid deliver device includes a housing; a reservoir disposed within the housing, the fluid reservoir defining a fluid outlet at a first end of the fluid reservoir; a plunger assembly disposed within the fluid reservoir, the plunger assembly including a friction clutch; and a seal engaged with an interior surface of the fluid reservoir to prevent movement of a material within the fluid reservoir past the seal; and a motive element in communication with a first end of the plunger assembly and configured to apply a motive force on the first end of the plunger assembly towards the first end of the fluid reservoir, wherein the friction clutch is configured to apply a frictional force to the interior surface of the fluid reservoir to resist the motive force, and wherein operation of the friction clutch enables motive force to overcome the frictional force to allow the plunger assembly to translate towards the first end of the fluid reservoir.

22 Claims, 6 Drawing Sheets

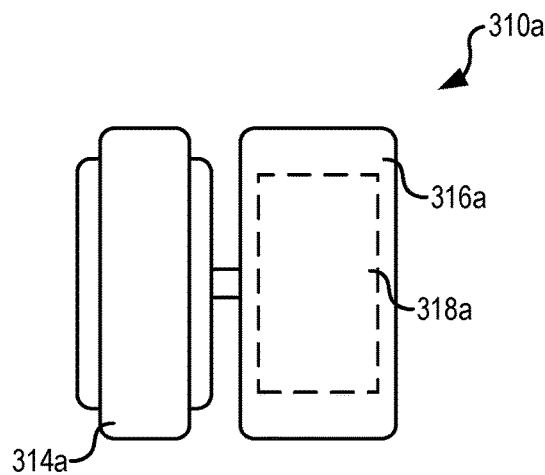
FIG. 3A
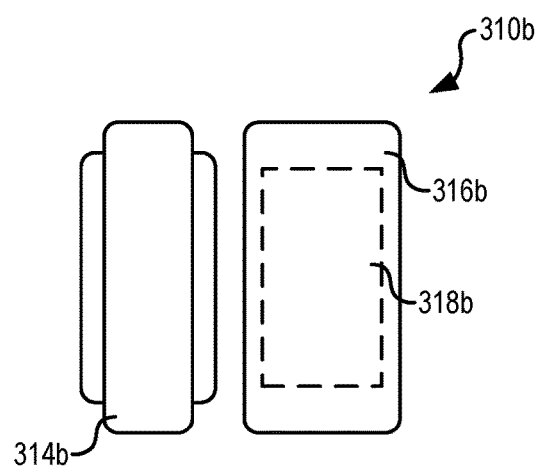
FIG. 3B
FIG. 3C
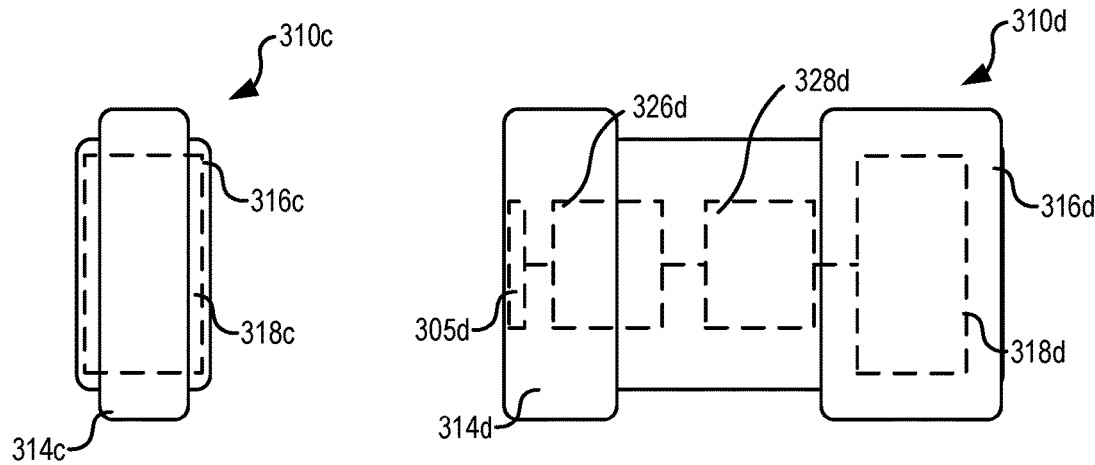
FIG. 3D

CLUTCHED DELIVERY DEVICE

PRIOR RELATED APPLICATION

This application claims priority to U.S. Provisional Application No. 62/452,511, filed Jan. 31, 2017, entitled "Clutched Delivery Device," which is hereby incorporated by reference in its entirety herein.

BACKGROUND

Fluid delivery devices enable delivery of medical fluids automatically using pumps, screw driven syringes, and other similar fluid displacement devices. These fluid displacement devices often include motors and/or gear boxes, which may limit the degree to which they can be miniaturized. Additionally, in some examples, manufacturing costs associated with such fluid displacement devices may be prohibitive for single use implementation.

SUMMARY

Various examples are described relating to fluid delivery devices for delivering a fluid medication. For example, one disclosed device may include a housing including a reservoir, a plunger assembly, and a motive element. The plunger assembly, which includes a friction clutch and a seal, is disposed within the reservoir and includes a first end and a second end. The motive element is in communication with the first end of the plunger assembly. Operation of the friction clutch causes the plunger assembly to translate within the reservoir.

This illustrative example is mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 3A illustrates a side view of an example plunger assembly, according to at least one example.

FIG. 3B illustrates a side view of an example plunger assembly, according to at least one example.

FIG. 3C illustrates a side view of an example plunger assembly, according to at least one example.

FIG. 3D illustrates a side view of an example plunger assembly, according to at least one example.

DETAILED DESCRIPTION

Figure 1:
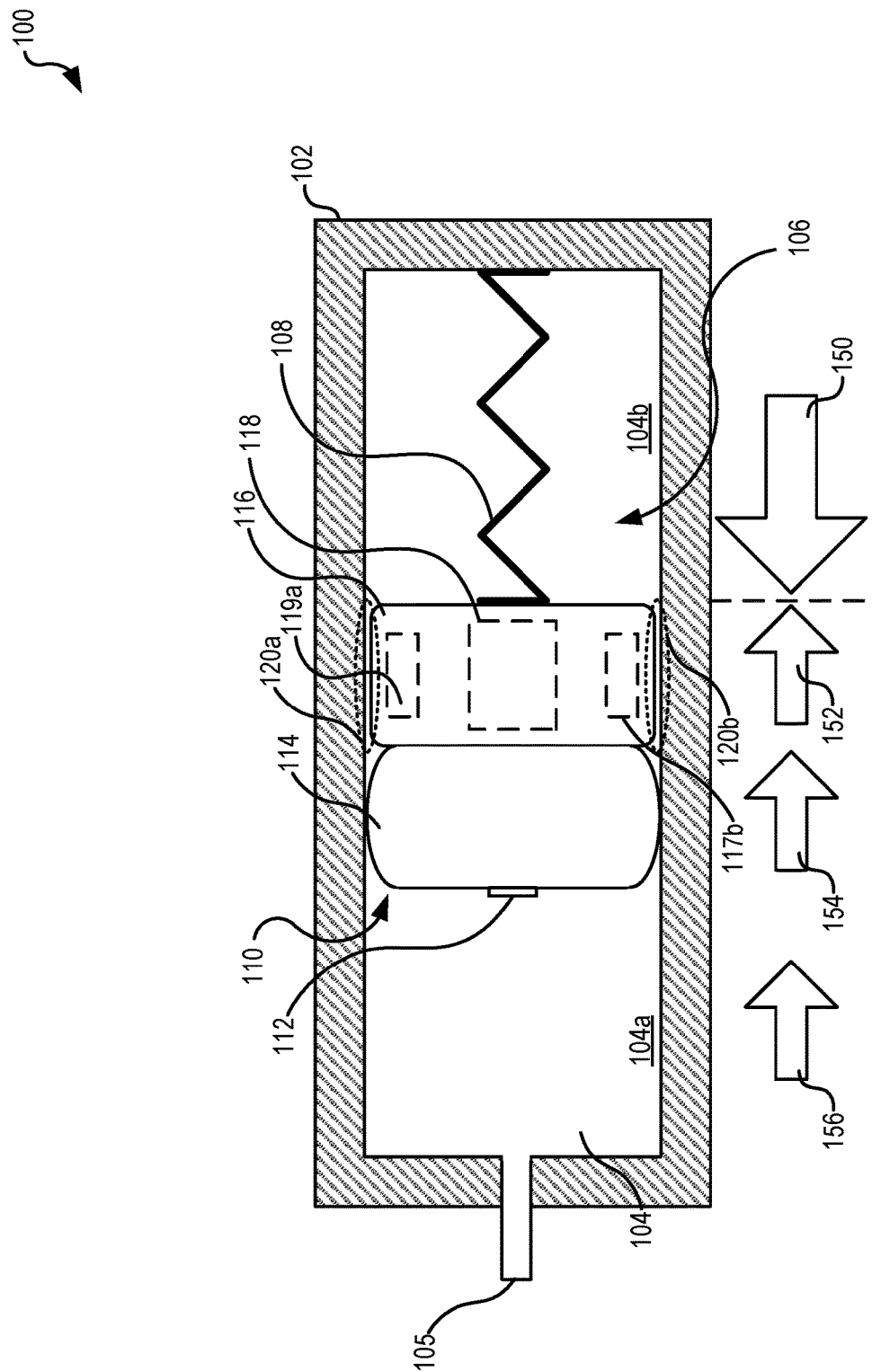
FIG. 1 illustrates a side view of an example fluid delivery device, according to at least one example.

Examples are described herein in the context of fluid delivery devices in the context of fluid medication delivery. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In one illustrative example, a fluid delivery device such as a disposable pen, belt worn pump, implantable pump, auto injector, ambulatory pump with an infusion set, or patch pump is configured to deliver fluid medication to a user. Instead of using conventional pumps or screw driven syringes for delivery, the fluid delivery device includes a motive plunger system located within a cylindrical reservoir of the fluid delivery device. Locating the motive plunger system within the reservoir saves space and enables miniaturization of this particular fluid delivery device. Such miniaturization may be especially beneficial for those fluid delivery devices that are designed to be wearable by users or implantable. Manufacturers of the fluid delivery devices may realize considerable cost savings as a result of the integrated design and function of the motive plunger system.

Beginning at a location adjacent to an outlet of the reservoir, the motive plunger system includes a plunger seal, a friction clutch, and a spring. The plunger seal engages with the curved inner surface of the reservoir to create a seal between the plunger seal and a portion of the reservoir including medication. This portion holds its largest volume when the device is full of medication. As the plunger seal is depressed into the reservoir, the medication is expelled from the reservoir. The spring is biased between a rear end (e.g., opposite the outlet) of the reservoir and the friction clutch. The spring pushes the friction clutch towards the outlet. The friction clutch frictionally engages with the curved inner surface of the reservoir and, together with other counter forces, effectively counters the force of the spring. Under these conditions, the system is at rest. To expel fluid, a vibratory element of friction clutch is activated. This vibratory element, formed from a piezo material, causes the friction clutch to begin to vibrate. This vibration reduces the effective coefficient of friction between the friction clutch and the curved inner surface. As a result, the force of the spring overcomes the opposing forces and pushes the plunger seal and the friction clutch toward the outlet. This causes the plunger seal and the friction clutch to translate lengthwise within the reservoir towards the outlet. In so doing, the plunger seal displaces the medication within the reservoir resulting in discharge of the medication at the outlet. After an amount of medication (e.g., a bolus dose of insulin, a series of boluses over time at approximately a continuous or variable rate, or other suitable dosage), has been discharged, the vibratory element is deactivated, restoring the original effective coefficient of friction between the friction clutch and the curved inner surface, causing the friction clutch to grip the curved inner surface with more force, thereby halting movement of the plunger seal.

This illustrative example is given to introduce the reader to the general subject matter discussed herein and the disclosure is not limited to this example. The following sections describe various additional non-limiting examples of fluid delivery devices.

Referring now to FIG. 1, FIG. 1 shows an example fluid delivery device 100. The fluid delivery device 100 includes a housing 102 that defines a fluid reservoir 104. The housing 102 can be formed from any suitable material including, for example, plastic, metal, glass, and other similar materials. The fluid reservoir 104 can have a generally cylindrical shape. For example, the fluid reservoir 104 can have an elliptical, oval, curvilinear, obround, square, polygonal, or other cross-sectional shapes that serve the same functions as described. The total volume of the fluid reservoir 104 is fixed, but this volume is distributed between portions 104a and 104b, depending on the location of a motive plunger system 106. For example, the motive plunger system 106, as described herein, is configured to translate within the fluid reservoir 104 to expel fluid from the fluid reservoir 104 via an outlet 105. This process of expelling fluid causes the volume of the portion 104a to reduce and the portion 104b to expand. The overall volume of the reservoir 104 however remains constant.

Figure 6:
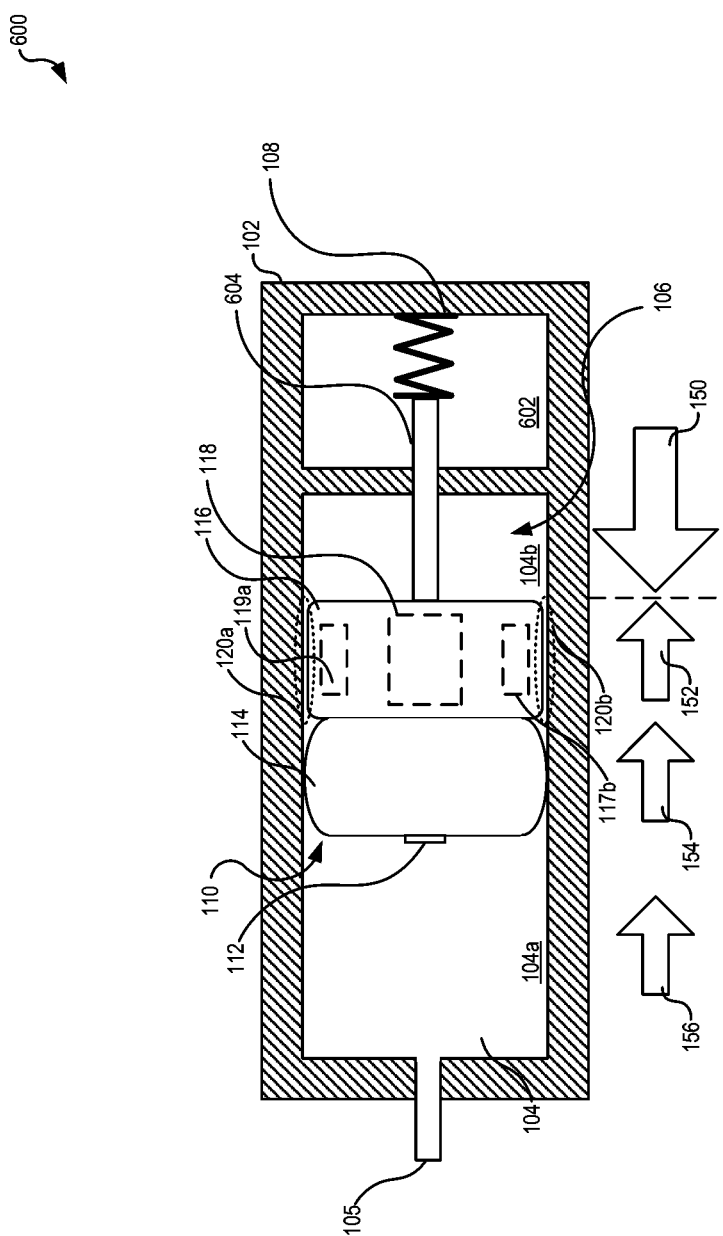
FIG. 6 illustrates a side view of an example fluid delivery device, according to at least one example.

The motive plunger system 106 includes a motive element 108 and a plunger assembly 110. Although in FIG. 1 the entirety of the motive plunger system 106 is illustrated within the fluid reservoir 104, it is understood that portions of the motive plunger system 106 can be disposed outside of the fluid reservoir 104. For example, as illustrated in FIG. 6 showing an example fluid delivery device 600, the motive element 108 can be disposed within a compartment 602 separate from the fluid reservoir 104 and connected to the plunger assembly 110 via a connecting rod 604.

The motive element 108 is biased to displace the plunger assembly 110. In the illustrated example, the motive element 108 is a spring biased between the plunger assembly 110 and a back wall of the fluid reservoir 104. Any suitable spring such as a compression spring, conical spring, volute spring, or other suitable spring can be used as the motive element 108. In some examples, the motive element 108 is a compressed gas, a compressed elastomer, a set of repelling magnets, or any other suitable element capable of exerting a motive force 150. The motive element 108 may be configured to apply a constant force along the length of the fluid reservoir 104. In some examples, control algorithms or sensors can be used to adjust performance of along the length of the fluid reservoir 104. The motive element 108 may be selected to be considerate of safety (e.g., to minimize fluid delivery rates).

The plunger assembly 110 includes a seal 114 and a friction clutch 116. The seal 114 is any suitable fluid seal including, for example, a wiper, an O-ring, a piston ring, and the like. The seal 114 extends radially towards and engages with the curved inner surface of the fluid reservoir 104. In this manner, the seal 114 functions as a plunger as the plunger assembly 110 translates within the fluid reservoir 104. The seal 114 can be attached to a solid structure, which can be attached to the friction clutch 116. While the seal 114 is illustrated as including a single seal, it is understood that the seal 114 can include more than one seal. For example, two or more seals (e.g., multiple O-rings) can be combined to form the seal 114. Increasing the number of seals can, in some examples, increase the overall opposing friction in the system.

The friction clutch 116 includes a vibratory element 118. The vibratory element 118 is any suitable element capable of producing a high-frequency vibration (e.g., 10-25 kHz) including, for example, an embedded piezo material or an eccentrically loaded motor. For example, any suitable piezoelectric ceramic material or crystal material may be used. Such materials include, for example, modified lead zirconate titanate ("PZT"), barium titanate, quartz, lead titanate, potassium niobate, sodium tungstate, zinc oxide, sodium potassium niobate, bismuth ferrite, sodium niobate, bismuth titanate, sodium bismuth titanate, and other suitable materials having the properties described herein.

The vibratory element 118 can be physically coupled to one or more clutch pads 119. The clutch pads 119 can function to transfer vibration energy away from the vibrating element 118. For example, the piezo material forming the vibrating element 118 can be arranged around the circumference of the friction clutch 116, with one or more clutch pads 119 in contact with the curved inner surface of the fluid reservoir 104. In some examples, the friction clutch 116 is formed as a short cylinder or other shape having a cross-section corresponding to the fluid reservoir 104. The vibratory element 118, which can also be formed a disk or cylinder, can be disposed in the center of the cylinder, with a set of clutch pads 119 circumferentially arranged about the vibratory element 118. The friction clutch 116 can be formed from a flexible material such as rubber or plastic. In some examples, an interior portion of the friction clutch 116 is formed from a rigid material that retains the vibratory element 118, and an exterior portion is formed from a flexible material. The clutch pads 119 can extend between the vibratory element 118 and a perimeter of the friction clutch 116 within the flexible material. The flexible material can include fluting disposed about its exterior surface to provide for expansion and contraction.

In some examples, the clutch pads 119a, 119b engage with the fluid reservoir 104 at areas 120a and 120b illustrated in FIG. 1. The clutch pad 119 can be formed from any suitable material including, for example, piezo material, rubber, glass, plastic, metal, and/or other suitable materials having the properties described herein. In some examples, the clutch pad material may be selected to minimize certain effects such as noise or undesired vibration modes, or optimize lubricity or friction effects. In some examples, a single bulk vibrating element 118 is included in the friction clutch 116 instead of or in addition to the clutch pads 119. In some examples, the vibratory element 118 is defined by multiple clutch pads 119 formed from piezo material. In this example, the individual clutch pads 119 can be selectively vibrated to achieve a finer degree of granularity in the movements of the friction clutch 116. For example, rotation of the friction clutch 116 or other complex motion can be achieved using the individual vibratory clutch pads 119. In some examples, the friction clutch 116 does not include the clutch pads 119. In this example, the vibratory element 118 may be in physical contact with the reservoir wall.

As described in further detail with reference to FIG. 2, the fluid delivery device 100 can also include any suitable power sources, control circuitry, and/or user interfaces to enable operation of the vibratory element 118 to enable movement of the plunger assembly 110. For example, as illustrated in FIG. 1, the plunger assembly 110 can also include a proximity sensor 122. The proximity sensor 112 is configured to detect its location with respect to the stroke of the plunger assembly 110. Sensor data from the proximity sensor 112 can be used to calculate flow rates for the fluid delivery device 100, total and remaining volume of the fluid reservoir 104, and any other suitable parameter relating to flow of the fluid delivery device 100.

The function of the fluid delivery device 100 will be explained with reference to forces 150-156 present within a system defined by the fluid reservoir 104. When the system is at rest, the sum of the downstream forces 152-156 is equal to the motive force 150. Because the forces are equal, the plunger assembly 110 does not move. The downstream forces 152-156 include a clutch friction force 152 corresponding to the friction between the friction clutch 116 and the inner surface of the fluid reservoir 104. The downstream forces 152-156 also include a seal friction force 154 corresponding to friction between the seal 114 and the inner surface of the fluid reservoir 104. The downstream forces 152-156 also include a fluid path resistance force 156 corresponding to fluid resistance in the fluid reservoir 104. When the vibratory element 118 within the friction clutch 116 is turned on, the friction clutch 116 (e.g., one or more clutch pads) begin to vibrate. This vibration causes a decrease in the effective coefficient of friction associated with clutch friction force 152 resulting in a decrease in the clutch friction force 152 (e.g., a low friction mode). Because of this reduction, the motive force 150 is sufficient to displace the plunger assembly 110 in the direction of the motive force 150. Fluid is dispensed via the outlet 105 as the plunger assembly 110 displaces within the fluid reservoir 104. Once the desired amount of fluid has been dispensed, the vibratory element 118 is turned off, increasing the effective coefficient of friction associated with the clutch friction force 152 and seizing movement of the plunger assembly 110 (e.g., a high friction mode).

In some examples, the flow rate via the outlet 105 is proportional to the duration that the friction clutch 116 is in the low friction mode. Various flow rates can be achieved by the fluid delivery device 100 by duty cycling the friction clutch 116 (e.g., cycling the vibratory element 118). In some examples, various flow rates can be achieved using a series of boluses, time between bolus, size of bolus, and other aspects of the boluses. The maximum flow rate may be determined by the magnitude of the motive element 108.

In some examples, the fluid delivery device 100 may be refillable. For example, a medication fluid may be introduced and/or reintroduced into the fluid reservoir 104 of the fluid delivery device 100 via the outlet 105. Suitable medication fluids may include insulin, epinephrine, naloxone, saline, etc. In this example, the pressure of the fluid acts upon and overcomes the friction clutch 116 and the motive element 108. These components translate in the opposite direction, refilling the fluid reservoir 104. In some examples, the friction clutch 1116 may be activated to reduce the opposing friction, reducing the input pressure required to fill the fluid reservoir 104.

Figure 2:
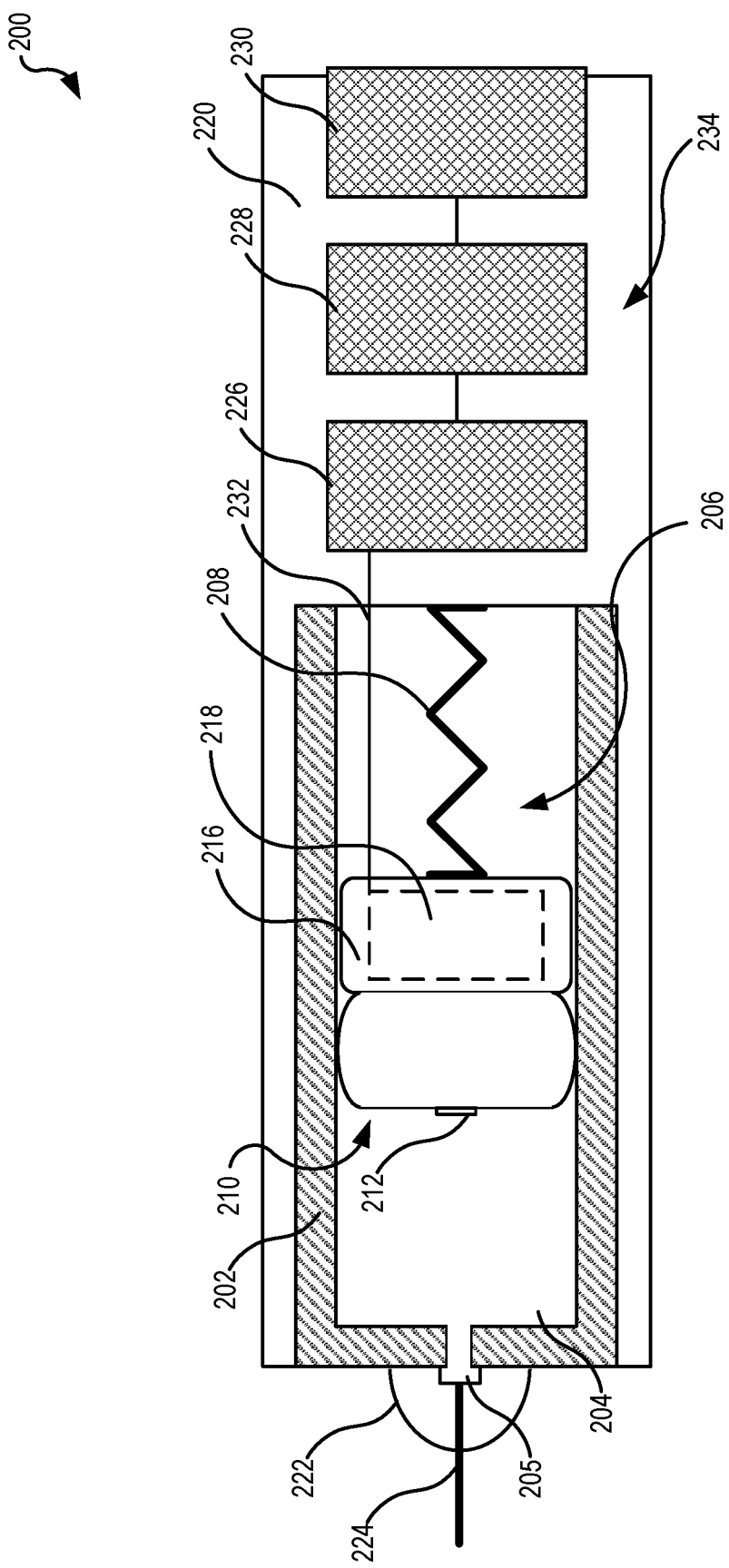
FIG. 2 illustrates a side view of an example fluid delivery device, according to at least one example.

FIG. 2 shows an example fluid delivery device 200. The fluid delivery device 200 is in the form factor of a fluid delivery pen. Thus, the fluid delivery device 200 includes a body 220 in which a housing 202 is housed. Like the fluid delivery device 100, the fluid delivery device 200 includes, a fluid reservoir 204, an outlet 205, and a motive plunger system 206 including a motive element 208 and a plunger assembly 210. The fluid delivery device 200 also includes a cannula 222 configured to receive a needle 224. The fluid delivery device 200 is configured to deliver fluid such as a fluid drug to a user via the needle 224. The outlet 205 may also include a septum to be pierced by the needle/cannula to enable single use disposable needles.

The fluid delivery device 200 also includes, within the housing 202, a power source 226, such as a battery, and control circuitry 228. The power source 226 is configured to provide power to the friction clutch 216 via wiring 232. The power source 226 also provides power to the control circuitry 228 via the wiring 232. The power source 226 is any suitable power source including, for example, single use batteries, rechargeable batteries, and other suitable power sources.

The control circuitry 228 includes one or more electronic components configured to manage the operation of the friction clutch 216 and other electronic elements of the fluid delivery device 200. Such components include, for example, a microcontroller, a memory, a timing source, one or more digital interfaces, one or more analog interfaces, voltage regulators, components for communicating information (e.g., radios and antennas, near field communication (NFC) chips, radio-frequency identification (RFID) systems, WiFi interface, cellular interface, Bluetooth Low Energy (BLE) chips, Bluetooth (BT) chips, and/or any other suitable component. The control circuitry 228 is configured to input particular waveforms to the vibratory element 118 to create the vibration. The control circuitry 228 is also configured to receive sensor data from the proximity sensor 212 and process the sensor data to determine flow rates, volumes, and the like relating to expulsion of fluid from the fluid reservoir 204.

In some examples, the control circuitry 228 includes a processing device and a computer-readable medium, such as a random access memory ("RAM") electrically coupled to the processing device. The processing device may execute computer-executable program instructions stored in the computer-readable medium, such as executing one or more computer programs. Such processing devices may include a microprocessor, a digital signal processor ("DSP"), an application-specific integrated circuit ("ASIC"), field programmable gate arrays ("FPGAs"), state machines, or other processing means for processing electrical signals received from sensors and interfaces of the fluid delivery device 200. Such processing means may also include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

The fluid delivery device 200 also includes a user interface 230. The power source 226, the control circuitry 228, and the user interface 230 are collectively referred to herein as auxiliary elements 234. The auxiliary elements 234 are coupled to the friction clutch 216 via the wiring 232. The user interface 230 is configured for user operation of at least some aspects of the fluid delivery device 200. For example, the user interface 230 can include a button, dial, knob, selector pad, or switch. A user can utilize the button or switch to power on and power off, pulse the friction clutch, and perform other user controls on the friction clutch 216 and/or the control circuitry 228. In some examples, the user interface 230 is used for user input (e.g., input an amount of medication to be delivered) and user output (e.g., output a percentage of medication remaining). For example, the user interface 230 can include a graphical user interface for displaying information about the fluid delivery device 200 (e.g., flow rate, volume remaining, dosage requirements, drug included in the fluid reservoir, status of the system, and other suitable information).

FIGS. 3A-3D show example plunger assemblies 310a, 310b, 310c, and 310d. The plunger assembly 310a includes a friction clutch 316a and a seal 314a. In this example, the friction clutch 316a is connected but isolated from the seal 314a. In this configuration, the friction clutch 316a can be manufactured separate from the seal 314a and combined during installation. The connection between the plunger assembly 310a can be suitably rigid such that, in practice, any force exerted on the friction clutch 316a from a motive element will be transferred via the connection to the seal 314a.

The plunger assembly 310b includes a friction clutch 316b and a seal 314b. In this example, the friction clutch 316b is separate from the seal 314b. In this configuration, the friction clutch 316b can be manufactured separate from the seal 314b. In practice, force exerted on the friction clutch 316b from a motive element will cause the friction clutch 316b (when in low friction mode) to displace towards the seal 314b. Once an inner face of the friction clutch 316b abuts against an opposing inner face of the seal 314b, the friction clutch 316b and the seal 314b will move together as a single unit. The seal 314b may be installed in the reservoir in one process and the clutch added during another process at different time (e.g., if the medication reservoir is manufactured filled and sealed separately from the device).

The plunger assembly 310c includes a friction clutch 316c and a seal 314c. In this example, the friction clutch 316c and the seal 314c are integrated into a single unit. In this example, clutch pads of a vibratory element 318c can engage with the seal 314 or with a separate seal. For example, the seal 314 can be formed from a material and in a manner such that even when the vibratory element 318c is actuated (e.g., in the low friction mode), the seal 314 continues to seal out fluid from the fluid reservoir. If a separate seal is provided, then the seal 314 can function to seal fluid and the separate seal can be in communication with the clutch pads to selectively engage with the inner surface of the fluid reservoir, depending on the operation of the vibratory element 318c.

The plunger assembly 310d includes a friction clutch 316c and a seal 314c. In this example, the friction clutch 316c and the seal 314c are integrated into a single unit. The plunger assembly 310d also includes a proximity sensor 305d, a power source 326d, control circuitry 328d, and a vibratory element 318d. The plunger assembly 310d can be considered a combined unit, the entirety of which can be installed within a fluid reservoir.

Figure 4:
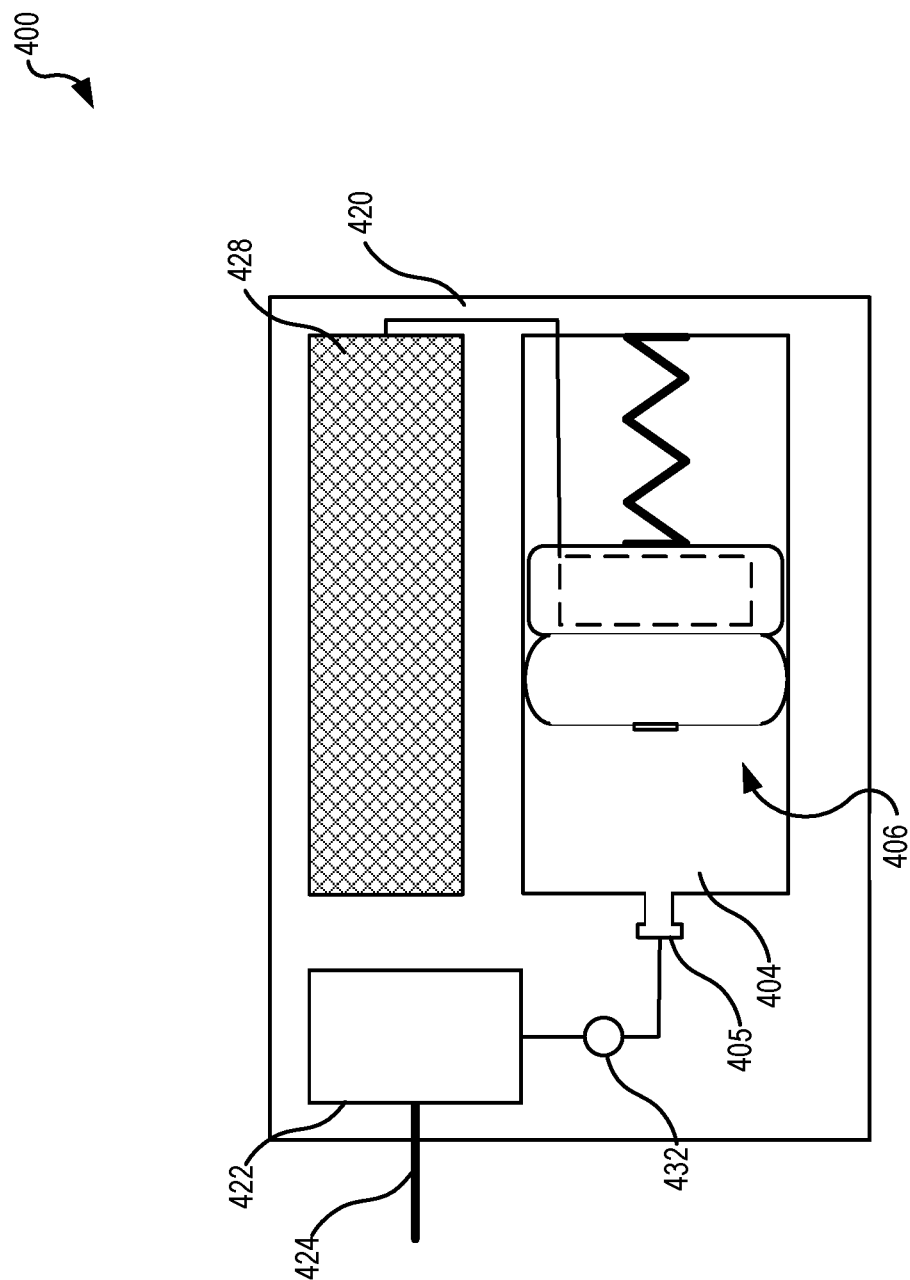
FIG. 4 illustrates an example fluid delivery device, according to at least one example.

FIG. 4 shows an example fluid delivery device 400. The fluid delivery device 400 is in the form factor of a continuous flow delivery device such as wearable insulin pump. Thus, the fluid delivery device 400 includes a housing 420, a fluid reservoir 404, and a motive plunger system 406. The fluid delivery device 400 also includes a cannula 422 configured to receive a needle 424. The fluid delivery device 400 is configured to deliver fluid such as a fluid drug to a user via the needle 424. The fluid delivery device 400 also includes an electronics/control area 428. The electronics/control area 428 includes a power source, control circuitry, sensors, user interfaces, radios, telemetry, and other suitable components for powering and controlling the fluid delivery device 400. The fluid delivery device 400 also includes a flow sensor 430 disposed between an outlet 405 and the cannula 422. The flow sensor 430 can be used to monitor the flow of fluids from the fluid reservoir 404 to the needle 424. The flow sensor 430 is in electrical communication with the electronics in the electronics/control area 428.

Figure 5:
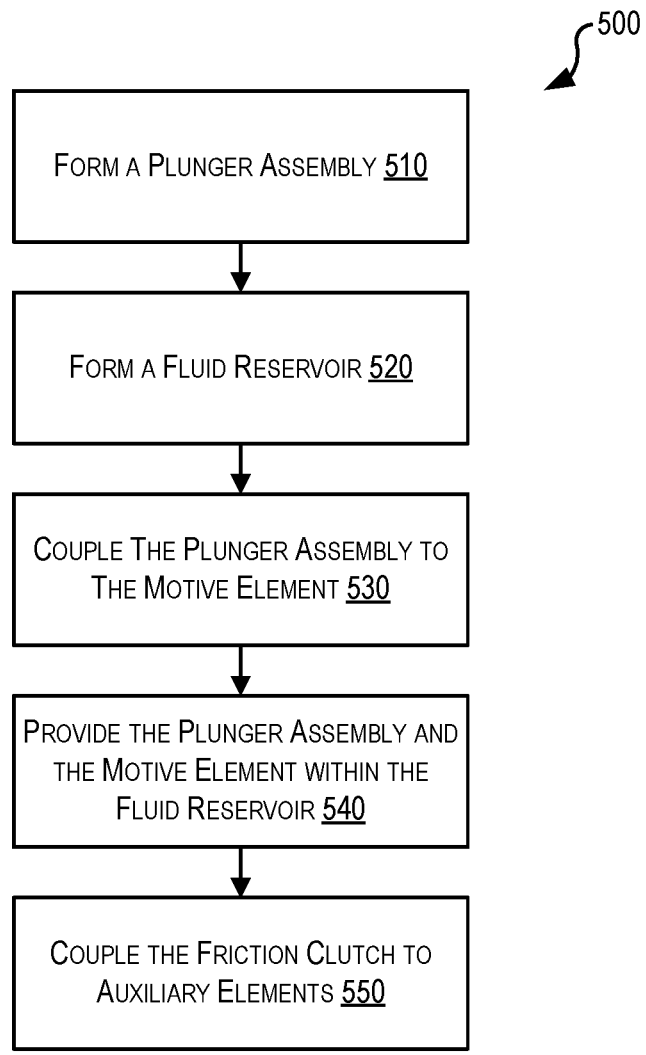
FIG. 5 illustrates an example method of manufacturing an example fluid delivery device, according to at least one example.

Referring now to FIG. 5, FIG. 5 shows an example method 500 for manufacturing a fluid delivery device. The method 500 will be described with respect to the example fluid delivery device 100 shown in FIG. 1, but may be used with any suitable fluid delivery device according to this disclosure.

At 510, a manufacture forms a plunger assembly 110. The plunger assembly 110, as described herein, includes a seal 114 and a friction clutch 116. The seal 114 is formed from any suitable material(s) capable of providing a fluid seal within a fluid reservoir 104. For example, the seal 114 can include a rigid plastic portion formed from injection molding, casting, or other suitable methods, which is surrounded by a flexible portion formed from a deformable material such as rubber. The friction clutch 116 includes a vibratory element 118 formed from a piezo material. The vibratory element 118 can be supported within the friction clutch 116 by a rigid plastic portion formed from injection molding, casting, or other suitable methods. The vibratory element 118 can be coupled via vibration transfer members to clutch pads 119 disposed circumferentially about the vibratory element 118. The vibration transfer members are configured to transfer vibrations from the vibratory element 118 to the clutch pads 119. In some examples, a single bulk vibratory element is included in the friction clutch 116 instead of the clutch pads 119.

At 520, the manufacture forms a fluid reservoir 104. The fluid reservoir 104 can be formed by injection molding, casting, glass drawing/forming, or any other suitable forming method. The fluid reservoir 104 may also be a septum formed on the outlet end to be pierced by a cannula/needle. The fluid reservoir 104 can be formed to include an opening in one end to receive the plunger assembly 110 and a motive element 108. The opening can then be closed or otherwise plugged once the plunger assembly 110 and the motive element 108 are within the fluid reservoir 104. In some examples, the fluid reservoir 104 is formed around the plunger assembly 110 and the motive element 108. For example, the fluid reservoir 104 can be formed as two halves. These halves can then be brought together, with the plunger assembly 110 and the motive element 108 between the two halves, and welded along seams of the two halves to form the fluid reservoir 104.

At 530, the manufacture couples the plunger assembly 110 to the motive element 108. This can include biasing one end of the motive element 108 between one side of the plunger assembly 110 (e.g., at the friction clutch 116) and an inner wall of the fluid reservoir 104. Coupling the plunger assembly 110 to the motive element 108 can also include adding a compressed gas, a compressed elastomer, or a set of repelling magnets to a portion 104b of the fluid reservoir 104 to function as the motive element 108 as described at block 540.

At 540, the manufacture provides the motive element 108 and the plunger assembly 110 within the fluid reservoir 104. Providing the motive element 108 and the plunger assembly 110 can include obtaining a preformed spring and placing it in the fluid reservoir 104. Providing the motive element 108 and the plunger assembly 110 can also include adding a compressed gas, a compressed elastomer, or a set of repelling magnets to a portion 104b of the fluid reservoir 104 to function as the motive element 108. Providing the motive element 108 and the plunger assembly 110 within the fluid reservoir 104 can include placing the motive element 108 and the plunger assembly 110 in the fluid reservoir 104 via an opening in the fluid reservoir 104 or forming the fluid reservoir 104 around the motive element 108 and the plunger assembly 110, as described herein. In some examples, the blocks 530 and 540 are performed prior to block 520.

At 550, the manufacture couples the friction clutch 116 to auxiliary elements 234. This can include electrically coupling the friction clutch 116 to the auxiliary elements 234 via wiring 232. Electrically coupling the auxiliary elements 234 enables control of the friction clutch 118, including the vibratory element 118.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:

1. A device, comprising:
   a housing;
   a fluid reservoir disposed within the housing, the fluid reservoir defining a fluid outlet at a first end of the fluid reservoir;
   a plunger assembly disposed within the fluid reservoir, the plunger assembly comprising:
      a friction clutch comprising a vibratory element; and
      a seal engaged with an interior surface of the fluid reservoir to prevent movement of a material within the fluid reservoir past the seal; and
   a motive element in communication with a first end of the plunger assembly and configured to apply a motive force on the first end of the plunger assembly towards the first end of the fluid reservoir,
   wherein the friction clutch is configured to apply a frictional force to the interior surface of the fluid reservoir to resist the motive force, and wherein operation of the vibratory element of the friction clutch enables the motive force to overcome the frictional force to allow the plunger assembly to translate towards the first end of the fluid reservoir.

2. The device of claim 1, wherein the fluid reservoir comprises a substantially cylindrical cross section comprising the interior surface, an interior wall, and wherein the fluid outlet is opposite the interior wall.

3. The device of claim 2, wherein the motive element is disposed within the fluid reservoir and in communication with the interior wall.

4. The device of claim 2, wherein the motive element is disposed outside the fluid reservoir, the motive element in communication with the plunger assembly using a connecting rod.

5. The device of claim 2, wherein
   the motive element comprises a spring, a compressed gas, a compressed elastomer, or a set of repelling magnets.

6. The device of claim 1, the seal is a fluid seal that extends cylindrically around a perimeter of the plunger assembly.

7. The device of claim 1, wherein the friction clutch comprises
   a clutch pad in physical communication with the vibratory element and disposed between the vibratory element and an interior surface of the fluid reservoir, and wherein the vibratory element comprises a piezo element or an eccentrically loaded motor.

8. The device of claim 7, wherein the operation of the friction clutch:
   causes the vibratory element to vibrate; and
   the clutch pad to change from a steady state to a vibrating state, wherein the motive force exceeds the frictional force when the clutch pad is in the vibrating state.

9. The device of claim 1, wherein the plunger assembly is defined as at least two parts, a first part comprising the friction clutch and a second part comprising the seal.

10. The device of claim 1, wherein the plunger assembly is defined as a single part.

11. The device of claim 1, further comprising a fluid disposed within the fluid reservoir between a second end of the plunger assembly and the first end of the fluid reservoir, wherein the fluid applies a fluid force to the second end of the plunger assembly, and wherein operation of the friction clutch enables the motive force to overcome the frictional force and the fluid force to allow the plunger assembly to translate towards the first end of the fluid reservoir.

12. The device of claim 11, wherein the fluid comprises a fluid medication.

13. The device of claim 12, wherein the fluid medication comprises at least one of insulin, epinephrine, naloxone, or saline.

14. A method, comprising:
   disposing a fluid reservoir defining a fluid volume within a housing, the fluid reservoir defining a fluid opening at a first end of the fluid reservoir;
   disposing a plunger assembly within the fluid reservoir, the plunger assembly comprising a seal and a friction clutch, the seal and friction clutch engaging with an interior surface of the fluid reservoir, wherein the friction clutch comprises a vibratory element; and
   coupling a motive element to a first end of the plunger assembly and to a first wall of the fluid reservoir to provide a motive force on the plunger assembly towards the first end of the fluid reservoir, wherein the friction clutch is configured to apply a frictional force to the interior surface of the fluid reservoir to resist the motive force, wherein operation of the vibratory element of the friction clutch causes the motive force to exceed the frictional force.

15. The method of claim 14, further comprising coupling the friction clutch to one or more auxiliary elements.

16. The method of claim 14, further comprising filling a portion of the fluid reservoir between a first end with a fluid medication.

17. The method of claim 16, wherein the fluid medication comprises at least one of insulin, epinephrine, naloxone, or saline.

18. The method of claim 14, wherein coupling the motive element to the first end of the plunger assembly comprises coupling the motive element to a connecting rod and coupling the connecting rod to the plunger assembly, wherein the motive element is disposed within the housing outside the fluid reservoir.

19. The method of claim 14, wherein coupling the motive element to the first end of the plunger assembly comprises disposing the motive element within the fluid reservoir and coupling the motive element to an interior surface of the fluid reservoir.

20. The method of claim 14, wherein the friction clutch comprises
a clutch pad in physical communication with the vibratory element and disposed between the vibratory element and an interior surface of the fluid reservoir, and wherein the vibratory element comprises a piezo element or an eccentrically loaded motor.

21. The method of claim 20, wherein operation of the friction clutch:
causes the vibratory element to vibrate; and
causes the clutch pad to change from a steady state to a vibrating state, wherein the motive force exceeds the frictional force when the clutch pad is in the vibrating state.

22. The method of claim 14, wherein the plunger assembly is defined as at least two parts, a first part comprising the friction clutch and a second part comprising the seal.

* * * * *